United States Patent [19]

Wilk et al.

[11] Patent Number: 5,354,270
[45] Date of Patent: Oct. 11, 1994

[54] SURGICAL CLOSURE DISK AND BALLOON METHOD

[76] Inventors: Peter J. Wilk, 185 W. End Ave., New York, N.Y. 10023; James Z. Cinberg, 167 N. Ridgewood Rd., South Orange, N.J. 07079

[21] Appl. No.: 34,097

[22] Filed: Mar. 22, 1993

Related U.S. Application Data

[63] Continuation-in-part of Ser. No. 803,582, Dec. 9, 1991, Pat. No. 5,211,624.

[51] Int. Cl.$^5$ .......................................... A61M 31/00
[52] U.S. Cl. .................................. 604/49; 606/192; 604/96
[58] Field of Search ............... 604/49, 53, 96, 99, 604/117, 164; 606/191, 192, 193, 195

[56] References Cited

U.S. PATENT DOCUMENTS

| | | | |
|---|---|---|---|
| 3,039,468 | 6/1962 | Price | 604/49 |
| 3,253,594 | 5/1966 | Matthews et al. | 604/96 |
| 3,860,007 | 1/1975 | Binard et al. | 604/99 |
| 4,089,337 | 5/1978 | Kronner | 604/96 |
| 4,280,501 | 7/1981 | Foderick | 604/99 |
| 4,441,495 | 4/1984 | Hicswa | |
| 4,638,803 | 1/1987 | Rand | |
| 4,798,592 | 1/1989 | Parks | 604/49 |
| 4,836,204 | 6/1989 | Landymore et al. | 604/53 |
| 4,861,334 | 8/1989 | Nawaz | 604/49 |
| 4,981,471 | 1/1991 | Quinn et al. | 604/97 |
| 5,125,897 | 6/1992 | Quinn et al. | 604/99 |
| 5,176,697 | 1/1993 | Hasson et al. | 606/191 |

FOREIGN PATENT DOCUMENTS

| | | |
|---|---|---|
| 3837779 | 5/1989 | Fed. Rep. of Germany . |
| 9001969 | 3/1990 | PCT Int'l Appl. . |

*Primary Examiner*—John D. Yasko
*Assistant Examiner*—Anthony Gutowski
*Attorney, Agent, or Firm*—R. Neil Sudol; Henry D. Coleman

[57] ABSTRACT

A surgical closure device comprises an elongate tubular member having a balloon attached in a collapsed configuration to the tubular member at the distal end thereof. A disk is attached to the tubular member at the distal end thereof, proximally of the balloon. During a surgical operation, the distal end of the instrument, including the balloon but not the disk, is inserted through a perforation in an internal body organ of a patient. The balloon is inflated while inside the organ and presses a wall of the organ against the disk to effectively close the perforation. The tubular member may then be subjected to a suction force to enable evacuation of liquid from the organ. After the suctioning operation, the tube is clamped and severed, the balloon remaining at least temporarily attached to the organ.

6 Claims, 3 Drawing Sheets

SURGICAL CLOSURE DISK AND BALLOON METHOD

This application is a continuation-in-part of copending application Ser. No. 803,582 filed Dec. 9, 1991 (now U.S. Pat. No. 5,211,624).

BACKGROUND OF THE INVENTION

This invention relates to a surgical closure device. This invention also relates to a surgical method utilizing the closure device. The closure device and associated method are particularly useful in laparoscopic surgery.

Laparoscopy involves the piercing of the abdominal wall and the insertion of a tubular port member through the perforation. Various instruments may be inserted through the tubular member to perform surgical operations inside the abdomen.

Generally, upon the disposition of the first tubular member so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Laparoscopic surgery frequently requires the temporary closure of perforations in internal organs and body tissues. Such closure is in some cases especially critical. For example, if a gall bladder is inadvertently perforated during dissection thereof in laparoscopic surgery, bile is spilled, which potentially contaminates other organs and tissues in the abdominal cavity. It is imperative, therefore, that the perforation be closed immediately.

In a conventional technique for closing a perforated gall bladder, a clamp is attached to the organ at the perforation. A loop is then passed around the clamp and drawn shut. This technique is difficult and time consuming. Moreover, a significant quantity of bile generally escapes the bladder into the abdomen.

Another kind of surgery requiring closure of perforations in internal organs arises where a patient is a victim of violence. In such cases of trauma, it frequently happens that many organs have perforations through which blood flows at a high rate into the patient's abdominal cavity. The closure of such wounds must be effectuated as quickly and efficiently as possible to minimize blood loss and trauma to the patient.

OBJECT OF THE INVENTION

An object of the present invention is to provide a closure device which facilitates surgical closure operations.

Another object of the present invention is to provide such a closure device which can be used in laparoscopic surgery to close wounds or perforations in internal body organs of a patient.

Another, more particular, object of the present invention is to provide such a closure device which is easy and quick to use.

A further object of the present invention is to provide a new method for at least temporarily closing openings in a patient's internal body organs and tissues.

SUMMARY OF THE INVENTION

A surgical closure device comprises, in accordance with the present invention, an elongate rod-like member having a distal end, a proximal end, a longitudinal axis, and a balloon attached in a collapsed configuration to the rod-like member at the distal end thereof. The balloon is expandable from the collapsed configuration to an expanded configuration by an inflation mechanism or component operatively connected to the balloon. A disk is attached to the rod-like member at the distal end thereof, proximally of the balloon. The disk extends substantially transversely to the longitudinal axis of the rod-like member and is spaced from the balloon so as to enable a clamping of an organic membrane between the disk and the balloon upon an expansion thereof by the inflation component.

Pursuant to another feature of the present invention, the rod-like member is hollow and thereby takes the form of a tube. In addition, components are provided for subjecting the tube to a vacuum, thereby providing an evacuating suction force at the distal end. This feature of the invention enables, for example, bile to be removed from a gall bladder upon the sealing of a perforation in the bladder by the inflated balloon and the disk.

Preferably, the tube is made of a deformable material. In that event, upon the inflation of the balloon and the consequent sealing of the opening at which the balloon and the disk are disposed, and possibly after the evacuation of the respective organ through a suctioning operation as described above, the tube may be closed and severed. If the organ is being removed from the body, then the balloon closure device may be retained in the opening during the removal of the organ.

Pursuant to an additional feature of the present invention, the expanded configuration of the balloon is substantially annular. Accordingly, the balloon defines a center hole, the rod-like member traversing the center hole of the balloon.

Pursuant to another feature of the present invention, disk is a substantially rigid member.

A surgical closure method comprises, in accordance with the present invention, the steps of (a) providing an elongate rod-like member provided at a distal end with an expandable balloon in a collapsed configuration and a substantially rigid disk located proximally of the balloon, (b) inserting the distal end of the rod-like member and the balloon through an opening in a selected internal body organ or tissue of the patient, (c) maintaining the disk on an outer side of the internal body organ or tissue of the patient during the step of inserting, and (d) inflating the balloon from the collapsed configuration to an expanded configuration so that a portion of the selected internal body organ or tissue is sandwiched between the balloon and the disk, thereby at least temporarily closing the opening.

Where the rod-like member is hollow and takes the form of a tube, the surgical closure method further comprises the step of applying suction to the tube upon the inflation of the balloon. In addition, the tube may be crimped and severed upon completion of the suction application step. The severing of the tube removes the shaft of the tube from the surgical site and thus provides more space for other procedures in the event, for example, that the method is being used during abdominal surgery. During laparoscopic surgery, the removal of the proximal end portion of the tube frees a trocar sleeve for the insertion of another instrument.

In abdominal surgery, a distal portion of the rod-like member is inserted into a patient's abdominal cavity, through an aperture in an abdominal wall of a patient, prior to the insertion of the distal end of the rod-like member and the balloon through an opening in a selected internal body organ or tissue of the patient. In the more specialized case of laparoscopic surgery, a laparoscopic trocar sleeve is disposed in the aperture in the abdominal wall of the patient at the onset of the surgical procedure, the distal portion of the rod-like member being inserted through the trocar sleeve into the patient's abdominal cavity.

A method in accordance with the present invention is particularly useful in laparoscopic surgery. In such a procedure, a distal portion of the rod-like or tubular member is inserted into a patient's abdominal cavity, through an aperture in an abdominal wall of a patient, prior to the step of inserting the distal end of the rod-like member and the one of the balloons only through an opening in a selected internal body organ or tissue of the patient.

A surgical method and closure device in accordance with the present invention is useful in trauma cases to quickly close wounds through which blood is flowing out of the patient or into an internal body cavity. The closure devices remain temporarily in place until each of the individual wounds can be closed separately by conventional techniques.

A closure device and associated method in accordance with the present invention facilitates surgical closure operations and is particularly effective in laparoscopic surgery to close wounds or perforations in internal body organs of a patient. Of course, the clamping disk is limited in diameter by the size of the respective trocar sleeve and particularly by the diameter of the port at the proximal end of the sleeve.

DETAILED DESCRIPTION

Figure 1:
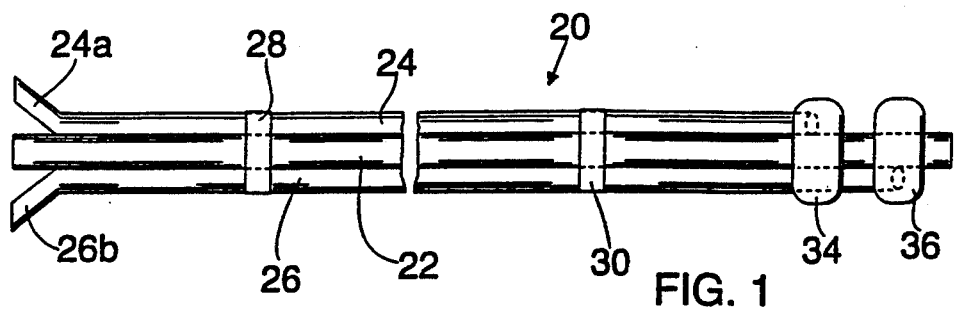
FIG. 1 is a side elevational view of a surgical closure device, showing a pair of balloons in a collapsed configuration.
Figure 2:
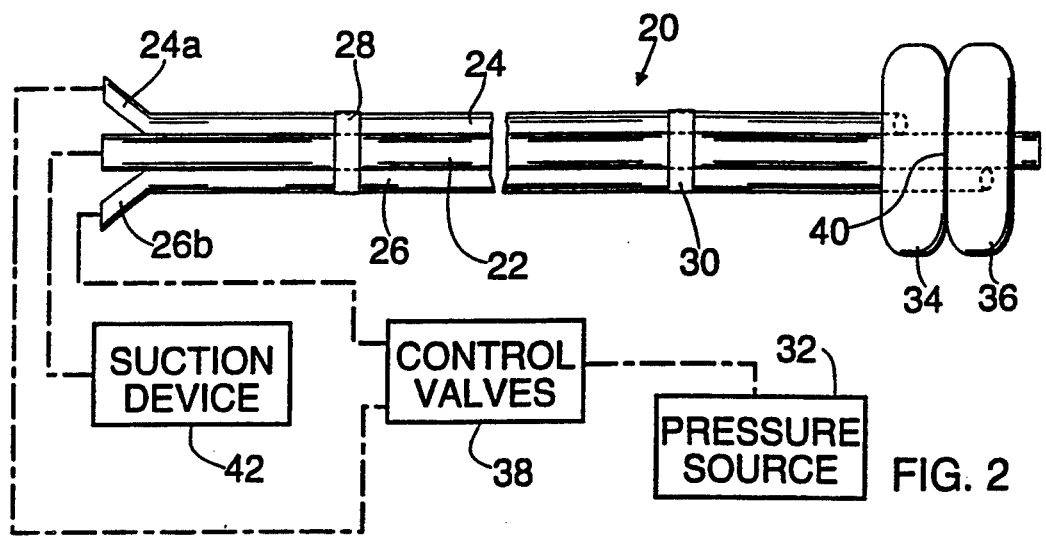
FIG. 2 is a side elevational view of the surgical closure device of FIG. 1, showing the balloons in an inflated or expanded configuration.

As illustrated in FIGS. 1 and 2, a surgical closure device 20 comprises a rod-like body member 22 in the form of an elongate substantially rigid tube. Two hollow conduits 24 and 26 are fastened to tube 22 via a plurality of clamping rings 28 and 30. Conduits 24 and 26 accordingly extend parallel to tube 22 from a proximal end of the instrument, where the conduits have end portions 24a and 26a which diverge from tube 22 to facilitate attachment of the conduits to a source of pressurized air 32.

At a distal end, conduits 24 and 26 communicate with respective annular balloons 34 and 36 which are initially in a collapsed or deflated configuration, as illustrated in FIG. 1. Balloons 34 and 36 are attached to tube 22, tube 22 traversing holes (not illustrated) at the centers of the balloons. Under the control of a valve assembly 38 which is connected between pressurized air source 32 and the proximal end portions 24a and 26a of conduits 24 and 26, balloons 34 and 36 are inflatable from the collapsed configuration of FIG. 1 to an expanded use configuration depicted in FIG. 2. In the expanded configuration, balloons 34 and 36 press tightly against one another along a contact plane 40.

Tube 22 is connectable at a proximal end to a suction device or vacuum generator 42, whereby a fluid or fluidized substance (liquid, gas, emulsion, suspension, powder, etc.) may be evacuated from a space at the distal end of tube 22.

It is to be noted that the structural relationship among tube 22 and conduits 24 and 26 may be varied within the scope of the invention. For example, conduits 24 and 26 may be located within tube 22 or may be formed by partitions inside tube 22. Alternatively, conduits 24 and 26 may be flexible tubular members generally separate from tube 22 and connected to tube 22 only indirectly via balloons 34 and 36 at the distal end of tube 22.

It is to be further noted that tube 22 is preferably rigid at least along a proximal end portion. At the distal end, tube 22 may be partially flexible to facilitate positioning and installation of balloons 34 and 36 at a perforation in an internal body organ of a patient. In that event, the closure device is provided with a plurality of tensioning cables (not shown) or other means for varying the orientation of the distal end of the instrument relative to the proximal end.

Figure 3A:
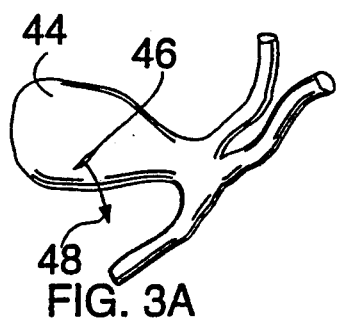
FIGS. 3A–3F show successive steps in the use of the closure device of FIGS. 1 and 2 to close a perforation in a gall bladder in a laparoscopic procedure.

FIG. 3A shows a gall bladder 44 with a perforation or opening 46. Bile is flowing out of the bladder, as indicated by an arrow 48.

Figure 3B:
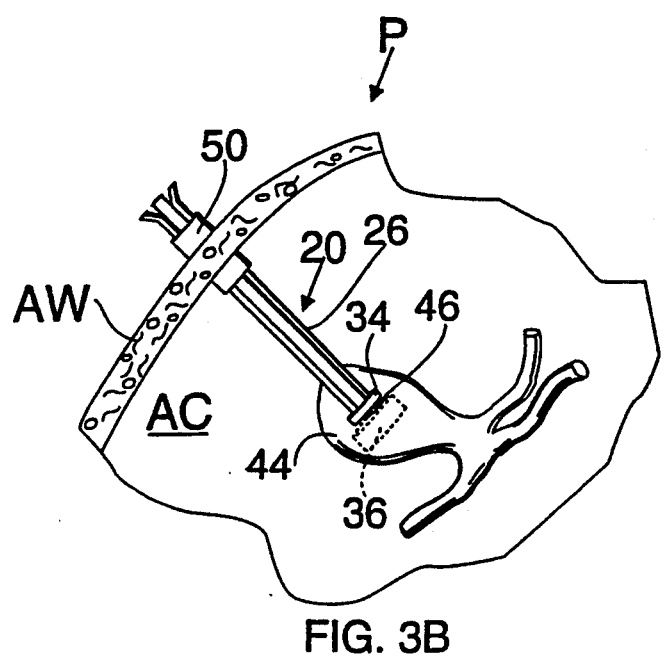

As illustrated in FIG. 3B, closure device 20 is partially inserted into the abdominal cavity AC of a patient P through a tubular port member 50 which is disposed in an opening (not visible) formed in the abdominal wall AW of the patient, for example, through the use of a trocar. The distal end of closure device 20 is inserted through opening 46 so that balloon 36 (located distally of balloon 34) is inserted into the bladder 44, while balloon 34 remains outside of the bladder. Conduit 26 is then connected to pressurized air source 32 (FIG. 2) via the opening of a valve in valve assembly 38, which pressurizes and inflates balloon 36 from the collapsed configuration of FIG. 1 to the expanded configuration shown in FIGS. 2 and 3B.

It is to be noted that pressurized air source 32 may take the form of a person's lungs, while control valves or valve assembly 38 includes the person's throat and/or lips. In addition, balloons 34 and 36 may be provided with one-way flow control valves (not illustrated) to prevent air from leaving the balloons once they are inflated. To deflate balloons 34 and 36 in that case, the operating surgeon need only pierce them with a scalpel or other sharp instrument.

Figure 3C:
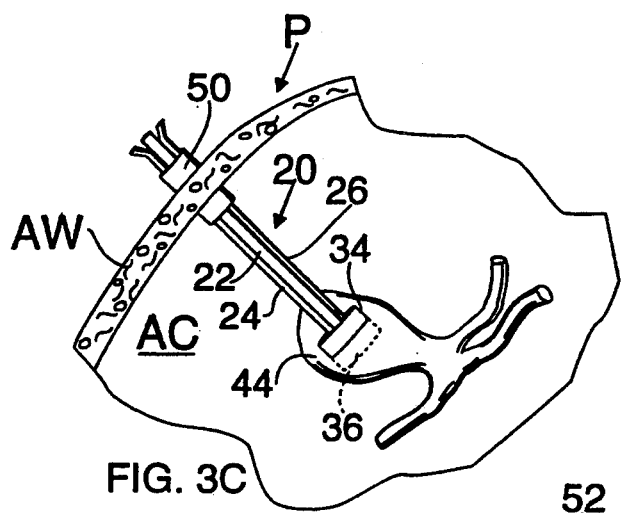

FIG. 3C depicts a subsequent stage in the laparoscopic operation utilizing the closure device of FIGS. 1 and 2. As shown in FIG. 3C, conduit 24 has been connected to pressurized air source 32 (FIG. 2) via the opening of a valve in valve assembly 38. Balloon 34 is thus inflated and presses against balloon 36 so as to tightly sandwich the wall of gall bladder 44 and effectively close opening 46.

Figure 3D:
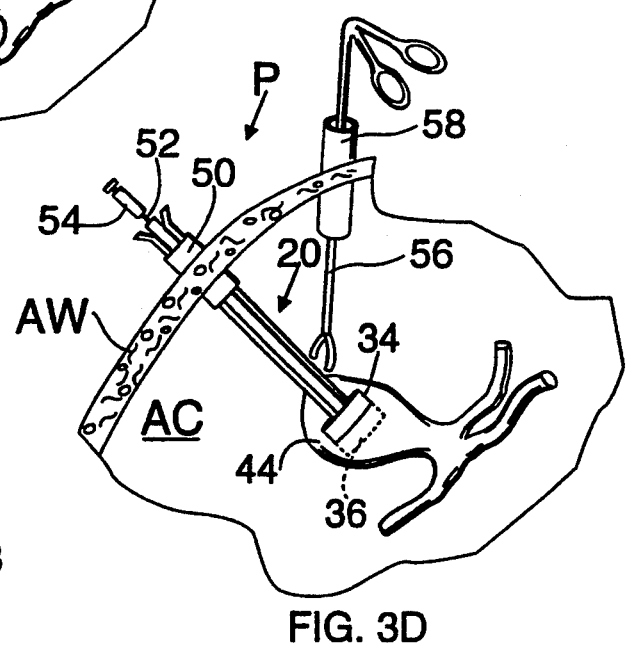

Upon the completed inflation of balloons 34 and 36, bile is aspirated from bladder 44, for example, through the connection of the proximal end of tube 22 to suction device 42 (FIG. 2) or through the insertion of another, thinner tube 52 through tube 22, as illustrated in FIG. 3D. Inner tube 52 is connected at a proximal end to a manually actuatable hypodermic syringe 54 or other source of underpressure.

Upon the completion of the suctioning operation, tube 22, as well as conduits 24 and 26, is closed at a point proximally located with respect to proximal balloon 34. This closure of tube 22 is effectuated with the aid of a clamping forceps 56 partially inserted into abdominal cavity AC through a second tubular port member 58 traversing abdominal wall AW. To facilitate a crimping of tube 22 by clamping forceps 56, at least a portion of tube 22 proximate to balloon 34 and located proximally thereof is made of a deformable material.

Figure 3E:
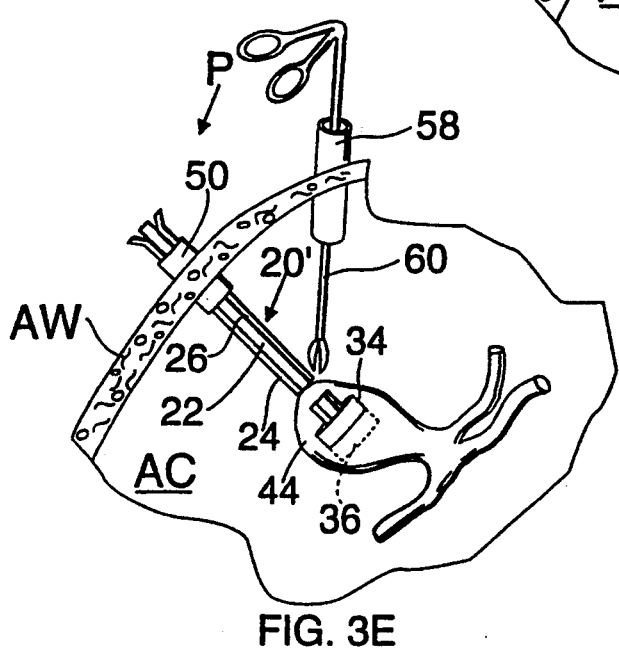
Figure 3F:
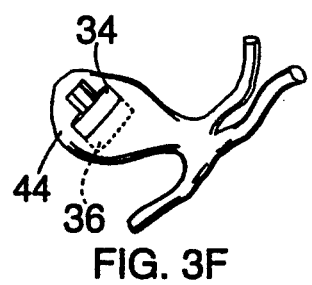

Upon a crimping of tube 22 (and optionally conduits 24 and 26), clamping forceps 56 is removed from abdominal cavity AC and a cutting forceps 60 is inserted for severing tube 22 and conduits 24 and 26 at a point located proximally with respect to the crimp, as shown in FIG. 3E. Cutting forceps 60 and the severed proximal end portion 20' of closure device 20 are then removed from abdominal cavity AC via port members 58 and 50, respectively. Balloons 34 and 36 remain attached at least temporarily to bladder 44, as illustrated in FIG. 3F, to maintain closure on perforation or opening 46.

Figure 4:
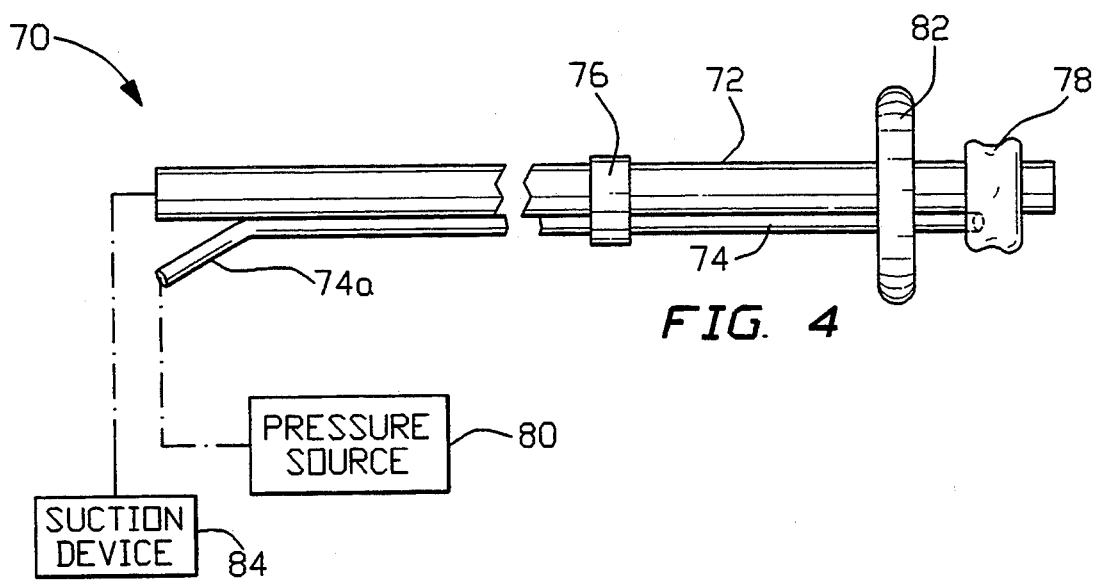
FIG. 4 is a side elevational view of a surgical closure device in accordance with the present invention, showing a balloon in a collapsed configuration and a disk at the distal end of a rod or tube.

As illustrated in FIG. 4, a surgical closure device 70 comprises a rod-like body member 72 in the form of an elongate substantially rigid tube. A hollow conduit 74 is fastened to tube 72 via a plurality of clamping rings 76. Conduit 74 extends parallel to tube 72 from a proximal end of the instrument, where the conduit has an end portion 74a which diverges from tube 72 to facilitate attachment of the conduits to a source of pressurized air 80.

At a distal end, conduit 74 communicates with an annular balloon 78 which is initially in a collapsed or deflated configuration. Balloon 78 is attached to tube 72, while tube 72 traverses a hole (not illustrated) at the center of the balloon. A pressurized air or saline solution source 80 is connected to conduit 74 at a proximal end thereof for expanding balloon 78 from the collapsed configuration of FIG. 1 to an expanded use configuration. In the expanded configuration, balloon 78 presses tightly against a substantially rigid disk 82 attached to tube 72 at a distal end thereof, proximally of balloon 78. Disk 82 has a diameter sufficiently small to enable the insertion of the distal end portion of the closure device 70 through a laparoscopic trocar sleeve during a laparoscopic procedure.

Tube 72 is connectable at a proximal end to a suction device or vacuum generator 84, whereby a fluid or fluidized substance (liquid, gas, emulsion, suspension, powder, etc.) may be evacuated from a space at the distal end of tube 72.

Conduit 74 may be located within tube 72 or may be formed by partitions inside tube 72. Alternatively, conduit 74 may be a flexible tubular member generally separate from tube 72 and connected to tube 72 only indirectly via balloon 78 at the distal end of tube 72.

It is to be further noted that tube 72 is preferably rigid at least along a proximal end portion. At the distal end, tube 72 may be partially flexible to facilitate positioning and installation of balloon 78 at a perforation in an internal body organ of a patient. In that event, the closure device is provided with a plurality of tensioning cables (not shown) or other means for varying the orientation of the distal end of the instrument relative to the proximal end.

The use of closure device 70 is substantially similar to the use of the device of FIGS. 1 and 2. Use of closure device 70 is clear from the description hereinabove with reference to FIGS. 3A-3F.

Figure 5:
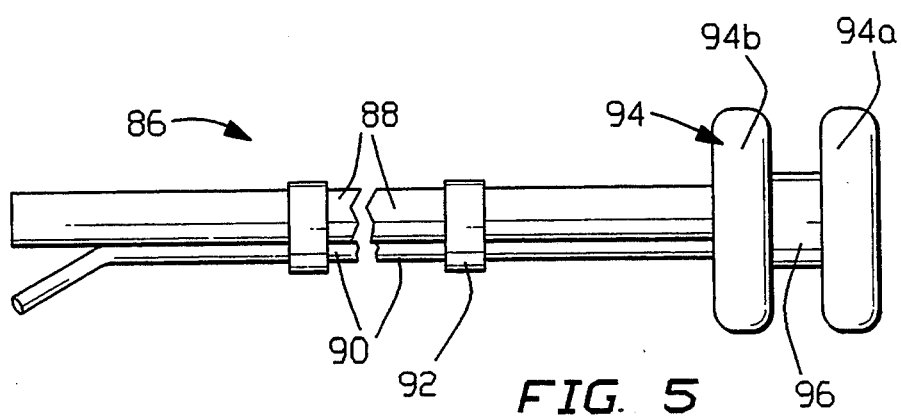
FIG. 5 is a side elevational view of another surgical closure device in accordance with the present invention, showing a balloon with a pair of intercommunicating lobes in a partially expanded configuration.

As illustrated in FIG. 5, a surgical closure device 86 comprises a rod-like body member 88 in the form of an elongate substantially rigid tube. A hollow conduit 90 is fastened to tube 88 via a plurality of clamping rings 92. Conduit 90 accordingly extends parallel to tube 88 from a proximal end of the instrument. At a distal end, conduit 90 communicates with a balloon 94 having a pair of annular lobes 94a and 94b connected to one another via an annular duct 96 or by a part of conduit 90. Annular balloon lobes 94a and 94b are initially in a collapsed or deflated configuration (compare FIG. 1). Duct 96 may be formed integrally with lobes 94a and 94b, as a unitary part of balloon 94.

Upon a pressurization of balloon 94, lobes 94a and 94b inflate substantially simultaneously to press or clamp an organic tissue membrane and thereby close a perforation through which the distal end of tube 88 and lobe 94a have been inserted during a surgical closure operation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A surgical closure method, comprising the steps of:
    disposing a laparoscopic trocar sleeve in an aperture in an abdominal wall of a patient;
    providing an elongate rod-like member provided at a distal end with an expandable balloon in a collapsed configuration and a substantially rigid disk located proximally of said balloon;
    moving said distal end of said rod-like member, said balloon in said collapsed configuration and said disk through said trocar sleeve into the patient's abdominal cavity;
    subsequently inserting said distal end of said rod-like member and said balloon through an opening in a selected internal body organ or tissue of the patient inside said abdominal cavity;
    maintaining said disk on an outer side of said internal body organ or tissue of the patient during said step of inserting; and inflating said balloon from said collapsed configuration to an expanded configuration so that a portion of the selected internal body organ or tissue is sandwiched between said balloon and said disk, thereby at least temporarily closing the opening.

2. The method defined in claim 1 wherein said rod-like member is hollow and takes the form of a tube, further comprising the step of applying suction to said tube upon completion of said step of inflating.

3. The method defined in claim 2, further comprising the step of crimping said tube upon completion of said step of applying suction.

4. The method defined in claim 3, further comprising the step of severing said tube proximally of said balloon upon completion of said step of crimping.

5. The method defined in claim 1, further comprising the step of severing said rod-like member proximally of balloon upon completion of said step of inflating.

6. The method defined in claim 1, further comprising the step of inserting into a patient's abdominal cavity, through an aperture in an abdominal wall of a patient, a distal portion of said rod-like member prior to the step of inserting the distal end of said rod-like member and said balloon through an opening in a selected internal body organ or tissue of the patient.

* * * * *